United States Patent
Liu et al.

(10) Patent No.: US 8,337,876 B2
(45) Date of Patent: Dec. 25, 2012

(54) DEVICES AND METHODS FOR TISSUE ENGINEERING

(75) Inventors: James Jenq Liu, Mason, OH (US); Adam Wallen, Swampscott, MA (US); Juha-Pekka Nuutinen, Tampere (FI)

(73) Assignee: Bio2 Technologies, Inc., Woburn, MA (US)

( * ) Notice: Subject to any disclaimer, the term of this patent is extended or adjusted under 35 U.S.C. 154(b) by 364 days.

(21) Appl. No.: 12/832,391

(22) Filed: Jul. 8, 2010

(65) Prior Publication Data
US 2011/0106255 A1 May 5, 2011

Related U.S. Application Data

(60) Provisional application No. 61/224,675, filed on Jul. 10, 2009, provisional application No. 61/234,768, filed on Aug. 18, 2009.

(51) Int. Cl.
*A61K 33/42* (2006.01)

(52) U.S. Cl. .................. 424/423; 623/13.18; 428/293.4

(58) Field of Classification Search .................. 424/423; 623/13.18; 428/293.4
See application file for complete search history.

(56) References Cited

U.S. PATENT DOCUMENTS

| | | | |
|---|---|---|---|
| 4,604,097 A | 8/1986 | Graves, Jr. et al. | |
| 4,655,777 A | 4/1987 | Dunn et al. | |
| 5,236,458 A | 8/1993 | Ducheyne et al. | |
| 5,397,365 A | 3/1995 | Trentacosta | |
| 5,468,544 A | 11/1995 | Marcolongo et al. | |
| 5,629,186 A | 5/1997 | Yasukawa et al. | |
| 5,676,720 A | 10/1997 | Ducheyne et al. | |
| 5,721,049 A | 2/1998 | Marcolongo et al. | |
| 6,146,892 A | 11/2000 | Ma et al. | |
| 6,162,537 A | 12/2000 | Martin et al. | |
| 6,187,329 B1 | 2/2001 | Agrawal et al. | |
| 6,277,394 B1 | 8/2001 | Sierra | |
| 6,296,667 B1 | 10/2001 | Johnson et al. | |
| 6,406,498 B1 | 6/2002 | Tormala et al. | |
| 6,451,059 B1 | 9/2002 | Janas et al. | |
| 6,471,993 B1 | 10/2002 | Shastri et al. | |
| 6,626,950 B2 | 9/2003 | Brown et al. | |
| 7,005,135 B2 * | 2/2006 | Janas et al. ..................... | 424/422 |
| 7,166,133 B2 | 1/2007 | Evans et al. | |

(Continued)

FOREIGN PATENT DOCUMENTS
EP 0051955 5/1982
(Continued)

OTHER PUBLICATIONS

Hench, Larry L., et al., "Bioactive Materials for Tissue Engineering Scaffolds", In *"Future Strategies for Tissue and Organ Replacement"* edited by Polak, Julia M., et al., 1st ed., World Scientific Publishing Co., Chapt. 1, (Aug. 2002), 1-24.

Liebschner, M.A.K. et al., "Optimization of Bone Scaffold Engineering for Load Bearing Applications", *Topics in Tissue Engineering 2003*, Chapter 6, (2003).

Brown, Roger F., et al., "Growth and differentiation of osteoblastic cells on 13-93 bioactive glass fibers and scaffolds", *Acta Biomaterialia 4*, (2008), 387-396.

(Continued)

*Primary Examiner* — Paul Marcantoni (57) ABSTRACT

A resorbable tissue scaffold fabricated from bioactive glass fiber forms a rigid three-dimensional porous matrix having a bioactive composition. Porosity in the form of interconnected pore space is provided by the space between the bioactive glass fiber in the porous matrix. Strength of the bioresorbable matrix is provided by bioactive glass that fuses and bonds the bioactive glass fiber into the rigid three-dimensional matrix. The resorbable tissue scaffold supports tissue in-growth to provide osteoconductivity as a resorbable tissue scaffold, used for the repair of damaged and/or diseased bone tissue.

14 Claims, 6 Drawing Sheets

U.S. PATENT DOCUMENTS

| | | | |
|---|---|---|---|
| 7,235,107 | B2 | 6/2007 | Evans et al. |
| 7,241,316 | B2 | 7/2007 | Evans et al. |
| 7,241,486 | B2 * | 7/2007 | Pirhonen ............... 428/297.4 |
| 7,270,813 | B2 | 9/2007 | Shimp et al. |
| 8,287,896 | B2 * | 10/2012 | Jung et al. ............... 424/423 |
| 2001/0041325 | A1 | 11/2001 | Ylanen et al. |
| 2003/0147860 | A1 | 8/2003 | Marchosky |
| 2004/0006153 | A1 | 1/2004 | Seppala et al. |
| 2004/0009598 | A1 | 1/2004 | Hench et al. |
| 2005/0037978 | A1 | 2/2005 | Damien |
| 2005/0081750 | A1 | 4/2005 | Xu et al. |
| 2005/0118236 | A1 | 6/2005 | Qiu et al. |
| 2005/0147642 | A1 | 7/2005 | Laredo et al. |
| 2006/0093645 | A1 * | 5/2006 | Janas et al. ............... 424/423 |
| 2006/0216321 | A1 | 9/2006 | Lyu et al. |
| 2007/0055373 | A1 | 3/2007 | Hudgins et al. |
| 2007/0087059 | A1 | 4/2007 | Everaerts et al. |
| 2007/0098799 | A1 | 5/2007 | Zhang et al. |
| 2007/0107395 | A1 | 5/2007 | Zuberi et al. |
| 2007/0110819 | A1 | 5/2007 | Pastorello et al. |
| 2007/0123984 | A1 | 5/2007 | Hodorek |
| 2007/0162151 | A1 | 7/2007 | Chang et al. |
| 2007/0190108 | A1 | 8/2007 | Datta et al. |
| 2008/0081061 | A1 | 4/2008 | King et al. |
| 2008/0103605 | A1 | 5/2008 | Kadiyala et al. |
| 2008/0152687 | A1 | 6/2008 | Thorne |
| 2008/0286179 | A1 | 11/2008 | Liu et al. |
| 2009/0035511 | A1 | 2/2009 | Liu et al. |
| 2010/0179667 | A1 * | 7/2010 | Day et al. ............... 623/23.72 |
| 2011/0106255 | A1 | 5/2011 | Liu et al. |
| 2011/0106272 | A1 * | 5/2011 | Liu ............... 623/23.61 |

FOREIGN PATENT DOCUMENTS

| | | |
|---|---|---|
| WO | WO-86/04088 | 7/1986 |
| WO | WO-01/32072 | 5/2001 |
| WO | WO-01/73126 | 10/2001 |
| WO | WO-2006/118554 | 11/2006 |

OTHER PUBLICATIONS

Moimas, Loredana et al., "Rabbit pilot study on the resorbability of three-dimensional bioactive glass fibre scaffolds", *Acta Biomaterialia 2*, (2006), 191-199.

Barthelat, Francois "Biomimetics for next generation materials", *Phil. Trans R. Soc. A*, 365, (2007), 2907-2919.

Brink, Maria et al., "Compositional dependence of bioactivity of glasses in the system Na2O-K2O-MgO-CaO-B2O3-P2O5-SiO2", *J Biomed Mater Res*, 37, (1997), 114-121.

Brink, Maria "The influence of alkali and alkaline earths on the working range for bioactive glasses", *Journal of Biomedical Materials Research*, vol. 36, (1997), 109-117.

Karlsson, Kaj H., et al., "Thirty-five years of guided tissue engineering", *Journal of Non-Crystalline Solids*, 354, (2008), 717-721.

Itala, A et al., "Characterization of microrough bioactive glass surface: Surface reactions and osteoblast responses in vitro", *J Biomed Mater Res*, 62, (2002), 404-411.

Vedel, Erik "Predicting the Properties of Bioactive Glasses", *Abo Akademi University, Laboratory of Inorganic Chemistry, Academic Dissertation*, Report 08-01, (2008).

Arstila, Hanna et al., "Factors affecting crystallization of bioactive glasses", *Journal of the European Ceramic Society*, 27, (2007), 1543-1546.

Fu, Qiang et al., "Freeze Casting of Porous Hydroxyapatite Scaffolds. II. Sintering, Microstructure, and Mechanical Behavior", *J Biomed Mater Res*, Part B: Appl Biomater 86B, (2008), 514-522.

Fu, Qiang et al., "In vitro cellular response to hydroxyapatite scaffolds with oriented pore architectures", *Materials Science and Engineering C*, MSC-02642, (2009).

Fu, Qiang et al., "Mechanical and in vitro performance of 13-93 bioactive glass scaffolds prepared by a polymer foam replication technique", *Acta Biomaterialia*, 4, (2008), 1854-1864.

* cited by examiner

DEVICES AND METHODS FOR TISSUE ENGINEERING

CROSS-REFERENCE TO RELATED APPLICATIONS

This application claims the benefit of Provisional Application No. 61/224,675, filed Jul. 10, 2009, and Provisional Application No. 61/234,768, filed Aug. 18, 2009, both of which are incorporated herein by reference.

FIELD OF THE INVENTION

The present invention relates generally to the field of porous fibrous medical implants. More specifically, the invention relates to a bioactive fibrous implant having osteostimulative properties in applications of in vivo environments.

BACKGROUND OF THE INVENTION

Prosthetic devices are often required for repairing defects in bone tissue in surgical and orthopedic procedures. Prostheses are increasingly required for the replacement or repair of diseased or deteriorated bone tissue in an aging population and to enhance the body's own mechanism to produce rapid healing of musculoskeletal injuries resulting from severe trauma or degenerative disease.

Autografting and allografting procedures have been developed for the repair of bone defects. In autografting procedures, bone grafts are harvested from a donor site in the patient, for example from the iliac crest, to implant at the repair site, in order to promote regeneration of bone tissue. However, autografting procedures are particularly invasive, causing risk of infection and unnecessary pain and discomfort at the harvest site. In allografting procedures, bone grafts are used from a donor of the same species but the use of these materials can raise the risk of infection, disease transmission, and immune reactions, as well as religious objections. Accordingly, synthetic materials and methods for implanting synthetic materials have been sought as an alternative to autografting and allografting.

Synthetic prosthetic devices for the repair of defects in bone tissue have been developed in an attempt to provide a material with the mechanical properties of natural bone materials, while promoting bone tissue growth to provide a durable and permanent repair. Knowledge of the structure and biomechanical properties of bone, and an understanding of the bone healing process provides guidance on desired properties and characteristics of an ideal synthetic prosthetic device for bone repair. These characteristics include, but are not limited to: bioresorbability so that the device effectively dissolves in the body without harmful side effects; osteostimulation and/or osteoconductivity to promote bone tissue in-growth into the device as the wound heals; and load bearing or weight sharing to support the repair site yet exercise the tissue as the wound heals to promote a durable repair.

Materials developed to date have been successful in attaining at least some of the desired characteristics, but nearly all materials compromise at least some aspect of the bio-mechanical requirements of an ideal hard tissue scaffold.

BRIEF SUMMARY OF THE INVENTION

The present invention meets the objectives of an effective synthetic bone prosthetic for the repair of bone defects by providing a material that is bioresorbable, osteostimulative, and load bearing. The present invention provides a bioresorbable (i.e., resorbable) tissue scaffold of bioactive glass fiber with a bioactive glass bonding at least a portion of the fiber to form a rigid three dimensional porous matrix. The porous matrix has interconnected pore space with a pore size distribution in the range of about 10 µm to about 600 µm with porosity between 40% and 85% to provide osteoconductivity once implanted in bone tissue. Embodiments of the present invention include pore space in the range of about 50 µm and about 500 µm.

Methods of fabricating a synthetic bone prosthesis according to the present invention are also provided that include mixing bioactive fiber with a binder, a pore former, and a liquid to provide a plastically formable batch, and kneading the formable batch to distribute the bioactive fiber into a substantially homogeneous mass of intertangled and overlapping bioactive fiber. The formable batch is dried, heated to remove the binder and pore former, and heated to a bond formation temperature using a primary heat source and a secondary heat source to form bonds between the intertangled and overlapping bioactive glass fiber.

These and other features of the present invention will become apparent from a reading of the following descriptions and may be realized by means of the instrumentalities and combinations particularly pointed out in the appended claims.

BRIEF DESCRIPTION OF THE SEVERAL VIEWS OF THE DRAWING

The foregoing and other objects, features, and advantages of the invention will be apparent from the following detailed description of the several embodiments of the invention, as illustrated in the accompanying drawings in which like reference characters refer to the same parts throughout the different views. The drawings are not necessarily to scale, with emphasis instead being placed upon illustrating the principles of the invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

The present invention provides a synthetic prosthetic tissue scaffold for the repair of tissue defects. As used herein, the terms "synthetic prosthetic tissue scaffold" and "bone tissue scaffold" and "tissue scaffold" and "synthetic bone prosthetic" in various forms may be used interchangeably throughout. In an embodiment, the synthetic prosthetic tissue scaffold is bioresorbable once implanted in living tissue. In an embodiment, the synthetic prosthetic tissue scaffold is osteoconductive once implanted in living tissue. In an embodiment, the synthetic prosthetic tissue scaffold is osteostimulative once implanted in living tissue. In an embodiment, the synthetic prosthetic tissue scaffold is load bearing once implanted in living tissue.

Various types of synthetic implants have been developed for tissue engineering applications in an attempt to provide a synthetic prosthetic device that mimics the properties of natural bone tissue and promotes healing and repair of tissue. Metallic and bio-persistent structures have been developed to provide high strength in a porous structure that promotes the growth of new tissue. These materials however, are not bioresorbable and must either be removed in subsequent surgical procedures or left inside the body for the life of the patient. A disadvantage of bio-persistent metallic and biocompatible implants is that the high load bearing capability does not transfer to regenerated tissue surrounding the implant. When hard tissue is formed, stress loading results in a stronger tissue but the metallic implant shields the newly formed bone from receiving this stress. Stress shielding of bone tissue therefore results in weak bone tissue which can actually be resorbed by the body, which is an initiator of prosthesis loosening.

Implants into living tissue evoke a biological response dependent upon a number of factors, such as the composition of the implant. Biologically inactive materials are commonly encapsulated with fibrous tissue to isolate the implant from the host. Metals and most polymers produce this interfacial response, as do nearly inert ceramics, such as alumina or zirconia. Biologically active materials or bioactive materials, elicit a biological response that can produce an interfacial bond securing the implant material to the living tissue, much like the interface that is formed when natural tissue repairs itself. This interfacial bonding can lead to an interface that stabilizes the scaffold or implant in the bony bed and provide stress transfer from the scaffold across the bonded interface into the bone tissue. When loads are applied to the repair, the bone tissue including the regenerated bone tissue is stressed, thus limiting bone tissue resorption due to stress shielding. A bioresorbable material can elicit the same response as a bioactive material, but can also exhibit complete chemical degradation by body fluid.

The challenge in developing a resorbable tissue scaffold using biologically active and resorbable materials is to attain load bearing strength with porosity sufficient to promote the growth of bone tissue. Conventional bioactive bioglass and bioceramic materials in a porous form are not known to be inherently strong enough to provide load-bearing strength as a synthetic prosthesis or implant. Conventional bioactive materials prepared into a tissue scaffold with sufficient porosity to be osteostimulative have not exhibited load bearing strength. Similarly, conventional bioactive materials in a form that provides sufficient strength do not exhibit a pore structure that can be considered to be osteostimulative.

Fiber-based structures are generally known to provide inherently higher strength to weight ratios, given that the strength of an individual fiber can be significantly greater than powder-based or particle-based materials of the same composition. A fiber can be produced with relatively few discontinuities that contribute to the formation of stress concentrations for failure propagation. By contrast, a powder-based or particle-based material requires the formation of bonds between each of the adjoining particles, with each bond interface potentially creating a stress concentration. Furthermore, a fiber-based structure provides for stress relief and thus, greater strength, when the fiber-based structure is subjected to strain in that the failure of any one individual fiber does not propagate through adjacent fibers. Accordingly, a fiber-based structure exhibits superior mechanical strength properties over an equivalent size and porosity than a powder-based material of the same composition.

Bioactive fiber-based materials have been proposed for tissue engineering applications but these prior art materials compromise either the load bearing requirement or the osteostimulative properties. For example, the teachings of Marcolongo et al. (U.S. Pat. No. 5,645,934) disclose a braided bioactive glass fiber composite structure with a thermoplastic polymer to provide load bearing capability, but insufficient porosity to provide osteostimulation. Similarly, the teachings of Dunn et al. (U.S. Pat. No. 4,655,777) discloses a bioactive glass fiber reinforced bioactive polymer matrix to provide a load bearing hard tissue scaffold, that relies upon the dissolution of the bioactive polymer to facilitate in-growth of bone tissue as the surrounding bone heals. The teachings of Pirhonen (U.S. Pat. No. 7,241,486) disclose a porous bone filler material prepared by sintering bioactive glass fibers, but the resulting pore morphology is not well controlled to ensure osteoconductivity and/or osteostimulation when fabricated in a form having high strength for potentially load bearing applications.

The present invention provides a material for tissue engineering applications that is bioresorbable, with load bearing capability, and osteostimulative with a pore structure that can be controlled and optimized to promote the in-growth of bone.

Figure 1:
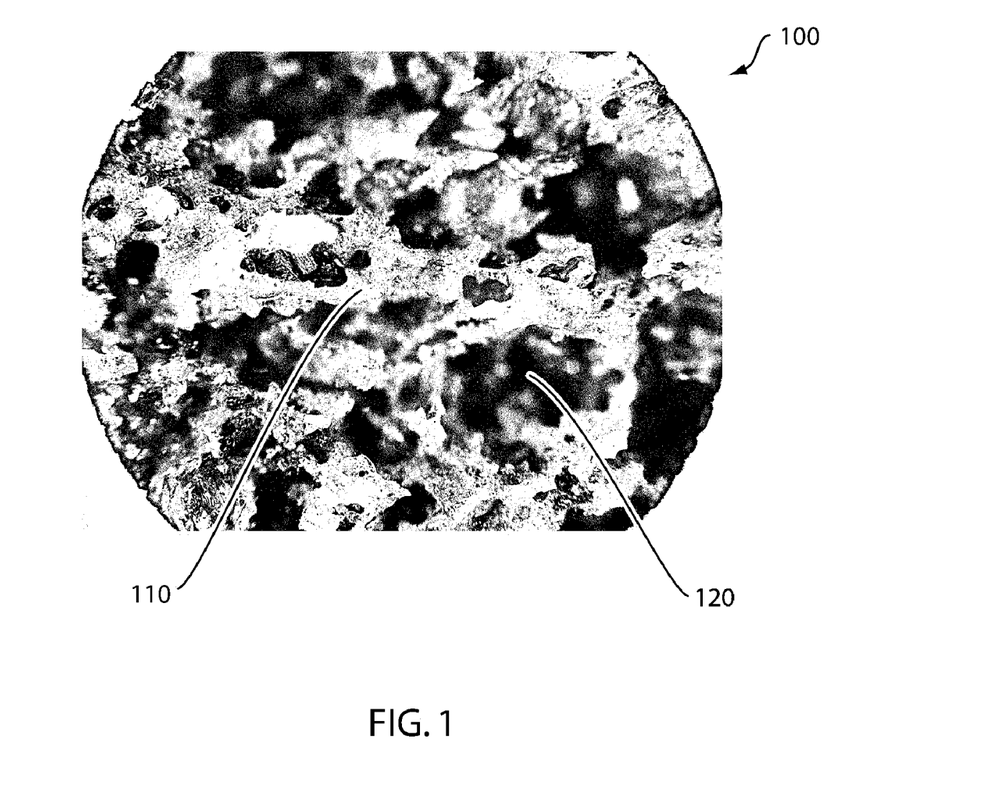
FIG. 1 is an optical micrograph at approximately 1000× magnification showing an embodiment of a bioactive tissue scaffold according to the present invention.

FIG. 1 is an optical micrograph at approximately 1000× magnification showing an embodiment of a bioactive tissue scaffold 100 of the present invention. The bioactive tissue scaffold 100 is a rigid three-dimensional matrix 110 forming a structure that mimics bone structure in strength and pore morphology. As used herein, the term "rigid" means the structure does not significantly yield upon the application of stress until it fractured in the same way that natural bone would be considered to be a rigid structure. The scaffold 100 is a porous material having a network of pores 120 that are generally interconnected. In an embodiment, the interconnected network of pores 120 provide osteoconductivity. As used herein, the term osteoconductive means that the material can facilitate the in-growth of bone tissue. Cancellous bone of a typical human has a compressive crush strength ranging between about 4 to about 12 MPa with an elastic modulus ranging between about 0.1 to about 0.5 GPa. As will be shown herein below, the bioactive tissue scaffold 100 of the present invention can provide a porous osteostimulative structure in a bioactive material with porosity greater than 50% and compressive crush strength greater than 4 MPa, up to, and exceeding 22 MPa.

In an embodiment, the three dimensional matrix 110 is formed from fibers that are bonded and fused into a rigid structure, with a composition that exhibits bioresorbability. The use of fibers as a raw material for creating the three dimensional matrix 110 provides a distinct advantage over the use of conventional bioactive or bioresorbable powder-based raw materials. In an embodiment, the fiber-based raw material provides a structure that has more strength at a given porosity than a powder-based structure. In an embodiment, the use of fibers as the primary raw material results in a bioactive material that exhibits more uniform and controlled dissolution rates in body fluid.

In an embodiment, the fiber-based material of the three-dimensional matrix 110 exhibits superior bioresorbability characteristics over the same compositions in a powder-based or particle-based system. For example, dissolution rates are increasingly variable and thus, unpredictable, when the material exhibits grain boundaries, such as a powder-based material form, or when the material is in a crystalline phase. Particle-based materials have been shown to exhibit rapid decrease in strength when dissolved by body fluids, exhibiting failures due to fatigue from crack propagation at the particle grain boundaries. Since bioactive glass or ceramic materials in fiber form are generally amorphous, and the heat treatment processes of the methods of the present invention can better control the amount and degree of ordered structure and crystallinity, the tissue scaffold 100 of the present invention can exhibit more controlled dissolution rates, with higher strength.

The bioactive tissue scaffold 100 of the present invention provides desired mechanical and chemical characteristics, combined with pore morphology to promote osteoconductivity. The network of pores 120 is the natural interconnected porosity resulting from the space between intertangled, nonwoven fiber material in a structure that mimics the structure of natural bone. Furthermore, using methods described herein, the pore size can be controlled, and optimized, to enhance the flow of blood and body fluid within of the scaffold 100 and regenerated bone. For example, pore size and pore size distribution can be controlled through the selection of pore formers and organic binders that are volatized during the formation of the scaffold 100. Pore size and pore size distribution can be determined by the particle size and particle size distribution of the pore former including a single mode of pore sizes, a bi-modal pore size distribution, and/or a multi-modal pore size distribution. The porosity of the scaffold 100 can be in the range of about 40% to about 85%. In an embodiment, this range promotes the process of osteoinduction of the regenerating tissue once implanted in living tissue while exhibiting load bearing strength.

The scaffold 100 is fabricated using fibers as a raw material. The fibers can be composed of a bioactive material that exhibits bioresorbability. The term "fiber" as used herein is meant to describe a filament in a continuous or discontinuous form having an aspect ratio greater than one, and formed from a fiber-forming process such as drawn, spun, blown, or other similar process typically used in the formation of fibrous materials. Bioactive fibers can be fabricated from a bioactive composition that is capable of being formed into a fiber form, such as bioactive glasses, ceramics, and glass-ceramics. The fibers can be fabricated from precursors of bioactive compositions, that form a bioactive composition upon formation of the three-dimensional matrix 110 while forming the scaffold 100.

Bioactive and bioresorbable glass materials are generally known as a glass having a composition of sodium carbonate, calcium carbonate, phosphorus pentoxide and silica, such as a glass composition having about 45-60 mol % silica and a 2-10 molar ratio of calcium to phosphate. Glass materials having this or a similar composition, demonstrate the formation of a silica-rich layer and a calcium phosphate film on the materials surface in an aqueous environment that readily bonds the glass material to bone. Compositional variations can be made, through the addition of compositions such as magnesia, potassium oxide, boric oxide, and other compounds, though it is generally known that a silica content between 45-60 mol % at the interfacial layer is advantageous to the formation of the silica-rich layer with the calcium phosphate film to promote the formation of bonds between the scaffold and the natural bone material. For example, see the publication of Ogino, Ohuchi, and Hench, "Compositional Dependence of the Formation of Calcium Phosphate Films on Bioglass", J Biomed Mater Res. 1980, 14:55-64 (incorporated herein by reference).

Glass compounds are more easily formed into a fiber form when the material can be melted and drawn into a fiber in an amorphous form. Bioactive and bioresorbable materials that can be fabricated into a fiber form without devitrification during the fiber drawing process require high silica content and both sodium oxide and potassium oxide to provide a mixed alkali effect to maintain an amorphous structure when formed into a fiber. Various compounds of mixed alkali and high-silica content glasses that can be easily pulled into fibers have demonstrated both bioactivity and bioresorbability. For example, see the publication of Brink, Turunen, Happonen, and Yli-Urpo, "Compositional Dependence of Bioactivity of Glasses in the System $Na_2O$—$K_2O$—$MgO$—$CaO$—$B_2O_3$—$P_2O_5$—$SiO_2$," J Biomed Mater Res. 1997; 37:114-121 (incorporated herein by reference), that describes at least ten different compositions in the $Na_2O$—$K_2O$—$MgO$—$CaO$—$B_2O_3$—$P_2O_5$—$SiO_2$ system that can be readily drawn into fiber and that demonstrate bioactivity. In an embodiment, a bioactive and bioresorbable material having a composition in respective mol % quantities of 6% $Na_2O$; 7.9% $K_2O$; 7.7% $MgO$; 22.1% $CaO$; 0% $B_2O_3$; 1.7% $P_2O_5$; and 54.6% $SiO_2$, (also referred to as 13-93 glass) provides bioactive and bioresorbability performance.

Referring still to FIG. 1, the network of pores 120 within the three-dimensional matrix 110 has a unique structure with properties that are particularly advantageous for the in-growth of bone tissue as a resorbable scaffold 100. The characteristics of the pore space 120 can be controlled through the selection of volatile components, as herein described below. Pore size and pore size distribution are important characteristics of the network of pores 120, that can be specified and controlled and thus, predetermined through the selection of volatile components having specific particle sizes and distributions to provide a structure that is osteoconductive, while maintaining strength for load bearing applications. Additionally, the network of pores 120 exhibits improved interconnectivity with large relative throat sizes between the pores due to the position of the fibers from the binder and pore former over the prior art materials that further enhances the osteoconductivity of the resorbable tissue scaffold 100 of the present invention. The network of pores 120 arises from the space resulting from the natural packing density of fibrous materials, and the space resulting from displacement of the fibers by volatile components mixed with the fiber during the formation of the resorbable scaffold 100. As further described below, the bioactive material forming the three dimensional matrix 110 is fabricated by fusing and bonding overlapping and intertangled fibers with a glass. The fibers and glass and/or glass precursors, are non-volatile components that are prepositioned through the formation of a homogeneous mixture with volatile components, such as binders and pore formers, including, for example, organic materials to predetermine the resulting pore size, pore distribution, and throat size between pores. Furthermore, the volatile components effectively increase the number of pore interconnections by increasing the throat size between pores resulting in pores being connected to multiple pores. Bulk fibers are deagglomerated and distributed throughout the mixture, resulting in a relative positioning of the fibrous materials in an overlapping and intertangled relationship within the volatile organic materials. Upon removal of the volatile components, and fusing and bonding of the fiber and glass to form the three-dimensional matrix 110, the network of pores 120 results from the space occupied by the volatile components.

An objective of a resorbable scaffold of the present invention is to facilitate in situ tissue generation as an implant within living tissue. While there are many criteria for an ideal scaffold for bone tissue repair, an important characteristic is a highly interconnected porous network with both pore sizes, and pore interconnections, large enough for cell migration, fluid exchange and eventually tissue in-growth and vascularization (e.g., penetration of blood vessels). The resorbable tissue scaffold 100 of the present invention is a porous structure with pore size and pore interconnectivity that is particularly adapted for the in-growth of bone tissue. The network of pores 120 has a pore size that can be controlled through the selection of volatile components used to fabricate the resorbable tissue scaffold 100, to provide an average pore size of at least 100 μm. Embodiments of the resorbable tissue scaffold 100 have an average pore size in the range of about 10 μm to about 600 μm, and alternatively, an average pore size in the range of about 100 μm to about 500 μm. The volatile components, including organic binder and pore formers, that form the pores, ensure a high degree of interconnectivity with large pore throat sizes within the three-dimensional matrix. It may be desirable to have a pore size distribution that is smaller than the pore size that may be determined through in vitro analysis, in that the pore size will increase as the three dimensional matrix 120 is dissolved and resorbed into the body. In this way, the load bearing capabilities of this material is enhanced upon initial implant, with the regenerated bone tissue bearing more of the load as it regenerates while the resorbable tissue scaffold 100 dissolves into the body.

Figure 2:
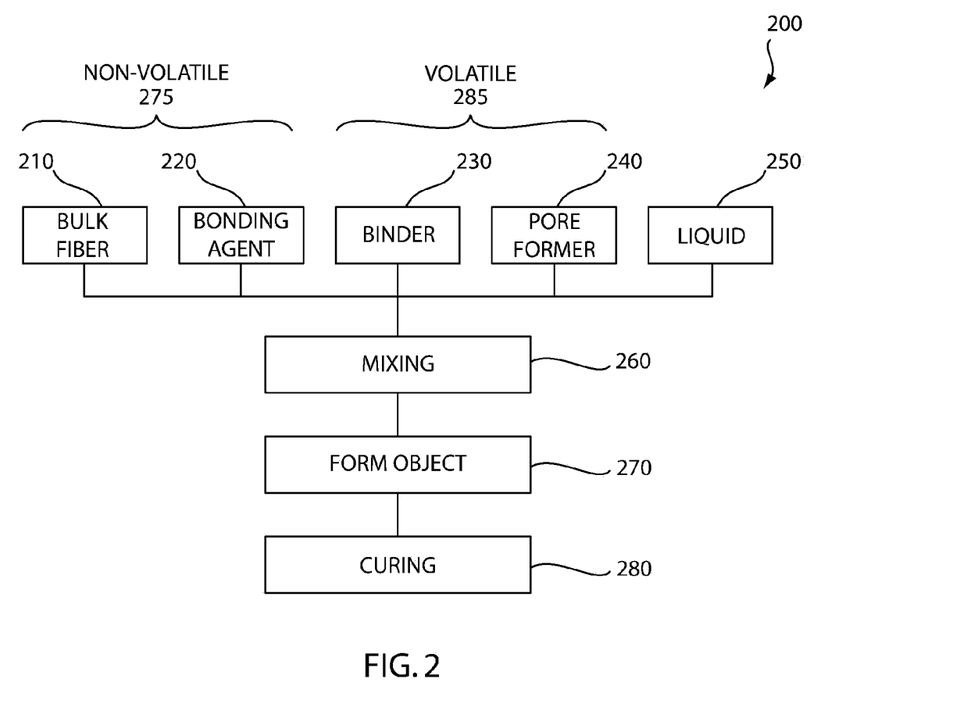
FIG. 2 is a flowchart of an embodiment of a method of the present invention for forming the bioactive tissue scaffold of FIG. 1.

Referring to FIG. 2, an embodiment of a method 200 of forming the bioactive tissue scaffold 100 is shown. Generally, bulk fibers 210 are mixed with a binder 230 and a liquid 250 to form a plastically moldable material, which is then cured to form the bioactive tissue scaffold 100. The curing step 280 selectively removes the volatile elements of the mixture, leaving the pore space 120 open and interconnected, and effectively fuses and bonds the fibers 210 into the rigid three-dimensional matrix 110.

The bulk fibers 210 can be provided in bulk form, or as chopped fibers. The diameter of the fiber 210 can range from about 1 to about 200 μm and typically between about 5 to about 100 μm. Fibers 210 of this type are typically produced with a relatively narrow and controlled distribution of fiber diameters, and fibers of a given diameter may be used, or a mixture of fibers having a range of fiber diameters can be used. The diameter of the fibers 210 will influence the resulting pore size and pore size distribution of the porous structure, as well as the size and thickness of the three-dimensional matrix 110, which will influence not only the osteoconductivity of the scaffold 100, but also the rate at which the scaffold 100 is dissolved by body fluids when implanted in living tissue and the resulting strength characteristics, including compressive strength and elastic modulus.

The binder 230 and the liquid 250, when mixed with the fiber 210, create a plastically formable batch mixture that enables the fibers 210 to be evenly distributed throughout the batch, while providing green strength to permit the batch material to be formed into the desired shape in the subsequent forming step 270. An organic binder material can be used as the binder 230, such as methylcellulose, hydroxypropyl methylcellulose (HPMC), ethylcellulose and combinations thereof. The binder 230 can include materials such as polyethylene, polypropylene, polybutene, polystyrene, polyvinyl acetate, polyester, isotactic polypropylene, atactic polypropylene, polysulphone, polyacetal polymers, polymethyl methacrylate, fumaron-indane copolymer, ethylene vinyl acetate copolymer, styrene-butadiene copolymer, acryl rubber, polyvinyl butyral, inomer resin, epoxy resin, nylon, phenol formaldehyde, phenol furfural, paraffin wax, wax emulsions, microcrystalline wax, celluloses, dextrines, chlorinated hydrocarbons, refined alginates, starches, gelatins, lignins, rubbers, acrylics, bitumens, casein, gums, albumins, proteins, glycols, hydroxyethyl cellulose, sodium carboxymethyl cellulose, polyvinyl alcohol, polyvinyl pyrrolidone, polyethylene oxide, polyacrylamides, polyethylerimine, agar, agarose, molasses, dextrines, starch, lignosulfonates, lignin liquor, sodium alginate, gum arabic, xanthan gum, gum tragacanth, gum karaya, locust bean gum, irish moss, scleroglucan, acrylics, and cationic galactomanan, or combinations thereof. Although several binders 230 are listed above, it will be appreciated that other binders may be used. The binder 230 provides the desired rheology of the plastic batch material in order to form a desired object and maintaining the relative position of the fibers 210 in the mixture while the object is formed, while remaining inert with respect to the bioactive materials. The physical properties of the binder 230 will influence the pore size and pore size distribution of the pore space 120 of the scaffold 100. Preferably, the binder 230 is capable of thermal disintegration, or selective dissolution, without impacting the chemical composition of the bioactive components, including the fiber 210.

The fluid 250 is added as needed to attain a desired rheology in the plastic batch material suitable for forming the plastic batch material into the desired object in the subsequent forming step 270. Water is typically used, though solvents of various types can be utilized. Rheological measurements can be made during the mixing step 260 to evaluate the plasticity and cohesive strength of the mixture prior to the forming step 270.

Pore formers 240 can be included in the mixture to enhance the pore space 120 of the bioactive scaffold 100. Pore formers are non-reactive materials that occupy volume in the plastic batch material during the mixing step 260 and the forming step 270. When used, the particle size and size distribution of the pore former 240 will influence the resulting pore size and pore size distribution of the pore space 120 of the scaffold 100. Particle sizes can typically range between about 25 μm or less to about 450 μm or more, or alternatively, the particle size for the pore former can be a function of the fibers 210 diameter ranging from about 0.1 to about 100 times the diameter of the fibers 210. The pore former 240 must be readily removable during the curing step 280 without significantly disrupting the relative position of the surrounding fibers 210.

In an embodiment of the invention, the pore former 240 can be removed via pyrolysis or thermal degradation, or volatization at elevated temperatures during the curing step 280. For example, microwax emulsions, phenolic resin particles, flour, starch, or carbon particles can be included in the mixture as the pore former 240. Other pore formers 240 can include carbon black, activated carbon, graphite flakes, synthetic graphite, wood flour, modified starch, celluloses, coconut shell husks, latex spheres, bird seeds, saw dust, pyrolyzable polymers, poly (alkyl methacrylate), polymethyl methacrylate, polyethyl methacrylate, poly n-butyl methacrylate, polyethers, poly tetrahydrofuran, poly (1,3-dioxolane), poly (alkalene oxides), polyethylene oxide, polypropylene oxide, methacrylate copolymers, polyisobutylene, polytrimethylene carbonate, poly ethylene oxalate, poly beta-propiolactone, poly delta-valerolactone, polyethylene carbonate, polypropylene carbonate, vinyl toluene/alpha-methylstyrene copolymer, styrene/alpha-methyl styrene copolymers, and olefin-sulfur dioxide copolymers. Pore formers 240 may be generally defined as organic or inorganic, with the organic typically burning off at a lower temperature than the inorganic. Although several pore formers 240 are listed above, it will be appreciated that other pore formers 240 may be used. Pore formers 240 can be, though need not be, fully biocompatible since they are removed from the scaffold 100 during processing.

A bonding agent 220 can be included in the mixture to promote strength and performance of the resulting bioactive scaffold 100. The bonding agent 220 can include powder-based material of the same composition as the bulk fiber 210, or it can include powder-based material of a different composition. As will be explained in further detail below, the bonding agent 220 based additives enhance the bonding strength of the intertangled fibers 210 forming the three-dimensional matrix 110 through the formation of bonds between adjacent and intersecting fibers 210. The bonding agent 220 can be bioactive glass, glass-ceramic, ceramic, or precursors thereto.

The relative quantities of the respective materials, including the bulk fiber 210, the binder 230, and the liquid 250 depend on the overall porosity desired in the bioactive tissue scaffold 100. For example, to provide a scaffold 100 having approximately 60% porosity, the nonvolatile components 275, such as the fiber 210, would amount to approximately 40% of the mixture by volume. The relative quantity of volatile components 285, such as the binder 230 and the liquid 250 would amount to approximately 60% of the mixture by volume, with the relative quantity of binder to liquid determined by the desired rheology of the mixture. Furthermore, to produce a scaffold 100 having porosity enhance by the pore former 240, the amount of the volatile components 285 is adjusted to include the volatile pore former 240. Similarly, to produce a scaffold 100 having strength enhanced by the bonding agent 220, the amount of the nonvolatile components 275 would be adjusted to include the nonvolatile bonding agent 220. It can be appreciated that the relative quantities of the nonvolatile components 275 and volatile components 285 and the resulting porosity of the scaffold 100 will vary as the material density may vary due to the reaction of the components during the curing step 280. Specific examples are provided herein below.

In the mixing step 260, the fiber 210, the binder 230, the liquid 250, the pore former 240 and/or the bonding agent 220, if included, are mixed into a homogeneous mass of a plastically deformable and uniform mixture. The mixing step 260 may include dry mixing, wet mixing, shear mixing, and kneading, which can be necessary to evenly distribute the material into a homogeneous mass while imparting the requisite shear forces to break up and distribute or de-agglomerate the fibers 210 with the non-fiber materials. The amount of mixing, shearing, and kneading, and duration of such mixing processes depends on the selection of fibers 210 and non-fiber materials, along with the selection of the type of mixing equipment used during the mixing step 260, in order to obtain a uniform and consistent distribution of the materials within the mixture, with the desired rheological properties for forming the object in the subsequent forming step 270. Mixing can be performed using industrial mixing equipment, such as batch mixers, shear mixers, and/or kneaders.

The forming step 270 forms the mixture from the mixing step 260 into the object that will become the bioactive tissue scaffold 100. The forming step 270 can include extrusion, rolling, pressure casting, or shaping into nearly any desired form in order to provide a roughly shaped object that can be cured in the curing step 280 to provide the scaffold 100. It can be appreciated that the final dimensions of the scaffold 100 may be different than the formed object at the forming step 270, due to expected shrinkage of the object during the curing step 280, and further machining and final shaping may be necessary to meet specified dimensional requirements. In an exemplary embodiment to provide samples for mechanical and in vitro and in vivo testing, the forming step 270 extrudes the mixture into a cylindrical rod using a piston extruder forcing the mixture through a round die.

Figure 3:
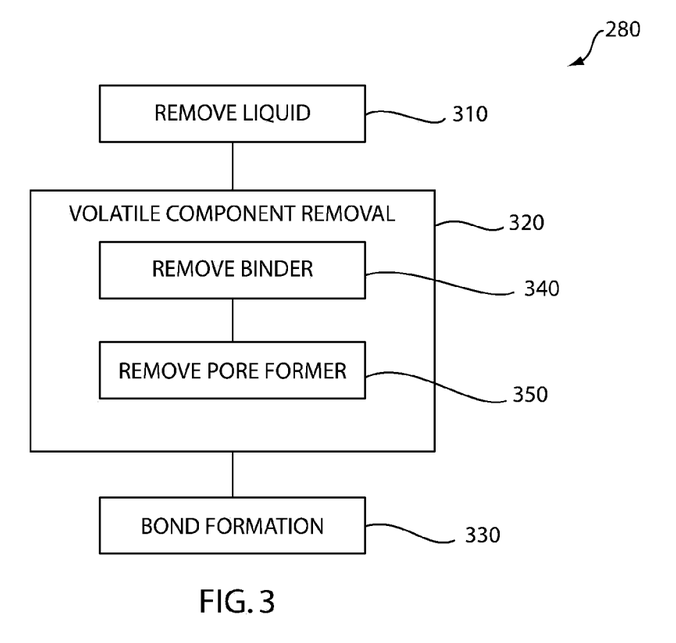
FIG. 3 is a flowchart of an embodiment of a curing step according to the method of FIG. 2 invention.

The object is then cured into the bioactive tissue scaffold 100 in the curing step 280, as further described in reference to FIG. 3. In the embodiment shown in FIG. 3, the curing step 280 can be performed as the sequence of three phases: a drying step 310; a volatile component removal step 320; and a bond formation step 330. In the first phase, drying 310, the formed object is dried by removing the liquid using slightly elevated temperature heat with or without forced convection to gradually remove the liquid. Various methods of heating the object can be used, including, but not limited to, heated air convection heating, vacuum freeze drying, solvent extraction, microwave or electromagnetic/radio frequency (RF) drying methods. The liquid within the formed object is preferably not removed too rapidly to avoid drying cracks due to shrinkage. Typically, for aqueous based systems, the formed object can be dried when exposed to temperatures between about 90° C. and about 150° C. for a period of about one hour, though the actual drying time may vary due to the size and shape of the object, with larger, more massive objects taking longer to dry. In the case of microwave or RF energy drying, the liquid itself, and/or other components of the object, adsorb the radiated energy to more evenly generate heat throughout the material. During the drying step 310, depending on the selection of materials used as the volatile components, the binder 230 can congeal or gel to provide greater green strength to provide rigidity and strength in the object for subsequent handling.

Once the object is dried, or substantially free of the liquid component 250 by the drying step 310, the next phase of the curing step 280 proceeds to the volatile component removal step 320. This phase removes the volatile components (e.g., the binder 230 and the pore former 240) from the object leaving only the non-volatile components that form the three-dimensional matrix 110 of the tissue scaffold 100. The volatile components can be removed, for example, through pyrolysis or by thermal degradation, or solvent extraction. The volatile component removal step 320 can be further parsed into a sequence of component removal steps, such as a binder burnout step 340 followed by a pore former removal step 350, when the volatile components 285 are selected such that the volatile component removal step 320 can sequentially remove the components. For example, HPMC used as a binder 230 will thermally decompose at approximately 300° C. A graphite pore former 220 will oxidize into carbon dioxide when heated to approximately 600° C. in the presence of oxygen. Similarly, flour or starch, when used as a pore former 220, will thermally decompose at temperatures between about 300° C. and about 600° C. Accordingly, the formed object composed of a binder 230 of HPMC and a pore former 220 of graphite particles, can be processed in the volatile component removal step 320 by subjecting the object to a two-step firing schedule to remove the binder 230 and then the pore former 220. In this example, the binder burnout step 340 can be performed at a temperature of at least about 300° C. but less than about 600° C. for a period of time. The pore former removal step 350 can then be performed by increasing the temperature to at least about 600° C. with the inclusion of oxygen into the heating chamber. This thermally-sequenced volatile component removal step 320 provides for a controlled removal of the volatile components 285 while maintaining the relative position of the non-volatile components 275 in the formed object.

Figure 4:
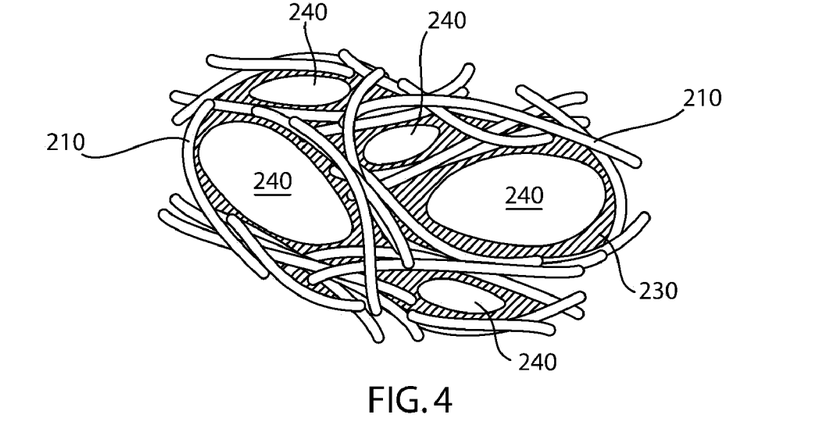
FIG. 4 is a schematic representation of an embodiment of an object fabricated according at a method of the present invention.
Figure 5:
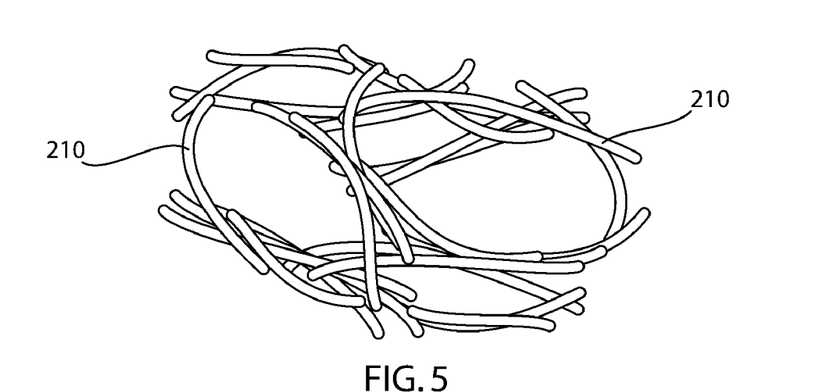
FIG. 5 is a schematic representation of the object of FIG. 4 upon completion of a volatile component removal step of the method of the present invention.

FIG. 4 depicts a schematic representation of the various components of the formed object prior to the volatile component removal step 320. The fibers 210 are intertangled within a mixture of the binder 230 and the pore former 240. Optionally, the bonding agent 220 can be further distributed in the mixture (not shown for clarity). FIG. 5 depicts a schematic representation of the formed object upon completion of the volatile component removal step 320. The fibers 210 maintain their relative position as determined from the mixture of the fibers 210 with the volatile components 285 as the volatile components 285 are removed. Upon completion of the removal of the volatile components 285, the mechanical strength of the object may be quite fragile, and handling of the object in this state should be performed with care. In an embodiment, each phase of the curing step 280 is performed in the same oven or kiln In an embodiment, a handling tray is provided upon which the object can be processed to minimize handling damage.

Figure 6:
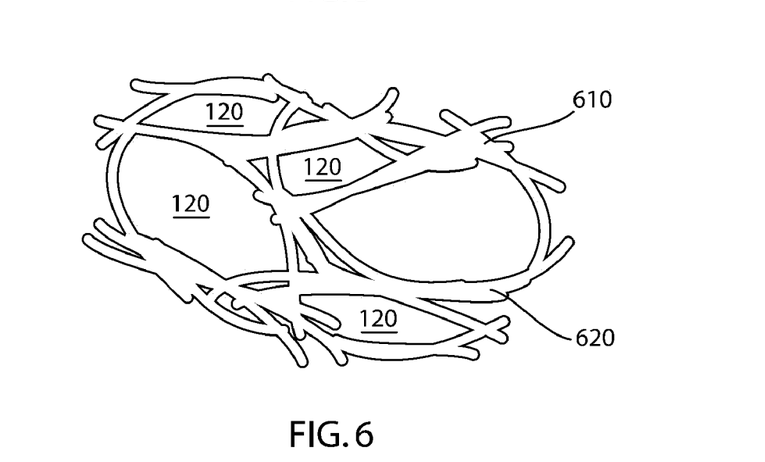
FIG. 6 is a schematic representation of the object of FIG. 5 upon completion of a bond formation step of the method of the present invention.

FIG. 6 depicts a schematic representation of the formed object upon completion of the last step of the curing step 280, bond formation 330. Pore space 120 is created where the binder 230 and the pore former 240 were removed, and the fibers 210 are fused and bonded into the three dimensional matrix 110. The characteristics of the volatile components 285, including the size of the pore former 240 and/or the distribution of particle sizes of the pore former 240 and/or the relative quantity of the binder 230, together cooperate to predetermine the resulting pore size, pore size distribution, and pore interconnectivity of the resulting tissue scaffold 100. The bonding agent 220 and the glass bonds that form at overlapping nodes 610 and adjacent nodes 620 of the three dimensional matrix 110 provide for structural integrity of the resulting three-dimensional matrix 110.

Figure 7:
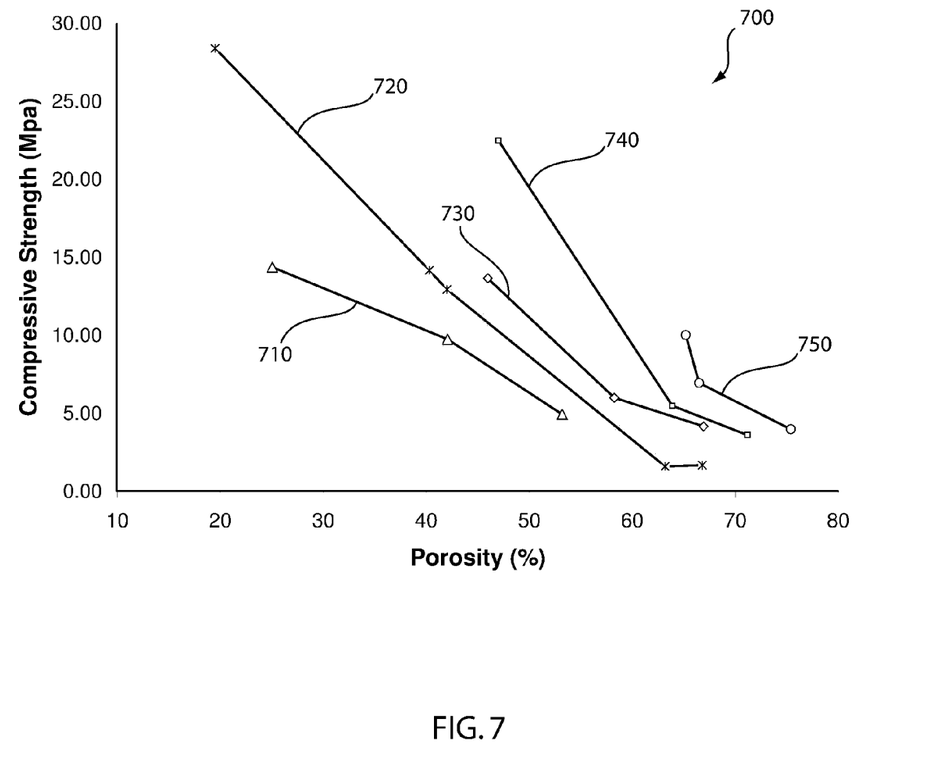
FIG. 7 is a graph of a comparative analysis of various embodiments of resorbable tissue scaffolds of the present invention compared to known samples.

To demonstrate the effect of the combination of the features of the present invention, a comparative analysis 700 is shown in FIG. 7. Five comparative samples (710, 720, 730, 740, and 750) were prepared and analyzed for compressive strength (in Mpa) and porosity (as a percentage). Sample 710 demonstrates the strength/porosity relationship for a powder-based porous structure of 13-93 bioactive glass. The sample 710 was prepared from a mixture of 5 grams of 13-93 bioactive glass powder, with 2 grams of HPMC organic binder, and water to provide a plastic batch, extruded into a 14 mm diameter rod, and sintered into a porous form at a plurality of sintering temperatures. The sample 720 was prepared from a mixture of 13-93 bioactive glass fiber with 2 grams of HPMC organic binder, and water to provide a plastic batch, extruded into a 14 mm diameter rod, and cured into a porous form at a plurality of bond formation temperatures, as described above with relation to FIG. 3. Both the sample 710 and the sample 720 did not include a pore former 240. As described above, the strength/porosity relationship for the fiber-based system of the sample 720 is improved over the powder-based sample 710. In sample 720, the organic binder, as a volatile component 285, positions the fiber with the space between the fibers predetermined by the volatile component 285 (here, the organic binder 230) to increase the porosity over a powder-based sample of the same effective strength.

To demonstrate the effect of the addition of a pore former 240, the sample 730 was prepared from a mixture of 13-93 bioactive glass powder with 2 grams HPMC organic binder and 1.5 grams of PMMA with a particle size of 100 µm as a pore former 240 and water to provide a plastic batch, extruded into a 14 mm diameter rod, and cured into a porous form at a plurality of sintering temperatures. Sample 740 was prepared from a mixture of 5 grams 13-93 bioactive glass fiber with 2 grams HPMC organic binder and 1.5 grams of PMMA with a particle size of 100 µm as a pore former 240 and water to provide a plastic batch, extruded into a 14 mm diameter rod, and cured into a porous form at a plurality of bond formation temperatures. Sample 750 was prepared from a mixture of 5 grams 13-93 bioactive glass fiber with 2 grams HPMC organic binder and 7 grams of 4015 graphite powder having a distribution of particle sizes of between about 150 to about 425 µm as a pore former 240, but with the addition of various quantities of 13-93 bioactive glass powder as a bonding agent 220, that was cured at a bond formation temperature of about 800° C. Again, the fiber based comparative samples 740 and 750 exhibit a strength/porosity relationship that exceeds the performance of the samples 710 and 730. The pore former 240 and the binder 230 cooperate to predetermine the resulting pore size, pore size distribution, and pore interconnectivity of the sample, with higher strength for a given porosity over conventional methods and devices.

Referring back to FIG. 3, the bond formation step 330 converts the nonvolatile components 275, including the bulk fiber 210, into the rigid three-dimensional matrix 110 of the bioactive tissue scaffold 100 while maintaining the pore space 120 created by the removal of the volatile components 275. The bond formation step 330 heats the non-volatile components 275 to a temperature upon which the bulk fibers 210 bond to adjacent and overlapping fibers 210, and for a duration sufficient to form the bonds, without melting the fibers 210, and thereby destroying the relative positioning of the non-volatile components 275. The bond formation temperature and duration depends on the chemical composition of the non-volatile components 275, including the bulk fiber 210. A bioactive glass fiber or powder of a particular composition exhibits softening and a capability for plastic deformation without fracture at a glass transition temperature. Glass materials typically have a devitrification temperature upon which the amorphous glass structure crystallizes. In an embodiment of the invention, the bond formation temperature in the bond formation step 330 is in the working range between the glass transition temperature and the devitrification temperature. For example the bond formation temperature for 13-93 bioactive glass composition can be above the glass transition temperature of about 606° C. and less than the devitrification temperature of about 851° C.

In the bond formation step 330, the formed object is heated to the bond formation temperature resulting in the formation of glass bonds at overlapping nodes 610 and adjacent nodes 620 of the fiber structure. The bonds are formed at overlapping nodes 610 and adjacent nodes 620 of the fiber structure through a reaction of the bonding agent 220 that flows around the fibers 210, reacting with the fibers 210 to form a glass coating and/or glass bonds. In the bond formation step 330, the material of the fibers 210 may participate in a chemical reaction with the bonding agent 220, or the fibers 210 may remain inert with respect to a reaction of the bonding agent 220. Further still, the bulk fibers 210 may be a mixture of fiber compositions, with a portion, or all of the fibers 210 participating in a reaction forming bonds to create the three-dimensional matrix 110.

The duration of the bond formation step 330 depends on the temperature profile during the bond formation step 330, in that the time at the bond formation temperature of the fibers 210 is limited to a relatively short duration so that the relative position of the non-volatile components 275, including the bulk fibers 210, does not significantly change. The pore size, pore size distribution, and interconnectivity between the pores in the formed object are determined by the relative position of the bulk fibers 210 by the volatile components 285. While the volatile components 285 are likely burned out of the formed object by the time the bond formation temperature is attained, the relative positioning of the fibers 210 and non-volatile components 275 are not significantly altered. The formed object will likely undergo slight or minor densification during the bond formation step 330, but the control of pore size and distribution of pore sizes can be maintained, and therefore predetermined by selecting a particle size for the pore former 240 that is slightly oversize or adjusting the relative quantity of the volatile components 285 to account for the expected densification.

In an embodiment of the invention, the bonding agent 220 is a bioactive glass material ground into a fine powder or nano-particle sizes (e.g., 1-100 nanometers). In this embodiment, the small particle sizes react more quickly at or near the glass transition temperature of the material composition, and form a glass that covers and bonds the overlapping nodes 610 and adjacent nodes 620 of the fiber structure before the fiber material is appreciably affected by the exposure to the temperature at or near its glass transition temperature. In this embodiment, for the bonding agent 220 to be more reactive than the bulk fibers 210, the particle size can be in the range of 1 to 1000 times smaller than the diameter of the fibers 210, for example, in the range of 10 microns to 10 nanometers when using 10 micron diameter bulk fibers 210. Nanoparticle sized powder can be produced by milling bioactive glass material in a milling or communication process, such as impact milling or attrition milling in a ball mill or media mill.

The temperature profile of the bond formation step 330 can be controlled to control the amount of crystallization and/or minimize the devitrification of the resulting three-dimensional matrix 110. As described above, bioactive glass and bioresorbable glass compounds exhibit more controlled and predictable dissolution rates in living tissue when the amount of accessible grain boundaries of the materials is minimized. These bioactive and bioresorbable materials exhibit superior performance as a bioactive device due to the amorphous structure of the material when fabricated into fibers 210, and the controlled degree of crystallinity that occurs during the heat treatment processing during the bond formation step 330. Therefore, in an embodiment of the method of the present invention, the temperature profile of the bond formation step 330 is adapted to bond the fiber structure without increasing grain boundaries in the non-volatile materials 275.

In an embodiment of the method of the present invention, the bond formation temperature exceeds the devitrification temperature of the bulk fibers 210 during the bond formation step 330. Compositions of bioactive glass can exhibit a narrow working range between its glass transition temperature and the crystallization temperature. In this embodiment, the crystallization of the fibers 210 may not be avoided in order to promote the formation of the bonds between overlapping and adjacent nodes of the fibers 210 in the structure. For example, bioactive glass in the 45S5 composition has an initial glass transition temperature of about 550° C. and a devitrification temperature of about 580° C. with crystallization temperatures of various phases at temperatures at about 610, about 800, and about 850° C. With such a narrow working range, the formation of a glass bond using the same composition as a bonding agent 220 is difficult to perform, and as such, the bond formation temperature may require bond formation temperatures in excess of about 900° C. to form the glass bonds. In an alternative embodiment, the bond formation temperature can exceed the crystallization temperature of the fibers 210, yet still fall within the working range of the composition of a bioactive glass in a powder form as a bonding agent 220. In this embodiment, the glass fibers 210 of a first composition may crystallize, with glass bonds of a second composition forming at overlapping and adjacent nodes of the fiber structure. For example a 13-93 composition in a powder form as a bonding agent 220 can be used with bioactive glass fibers in a 45S5 composition, to form a glass bond above the glass transition temperature of the 13-93 composition but less than the devitrification temperature of the 13-93 composition but exceeds the devitrification temperature of the 45S5 glass fiber composition to form a composite formed object.

In an embodiment of the invention, the temperature profile of the bond formation step 330 is configured to reach a bond formation temperature quickly and briefly, with rapid cooling to avoid devitrification of the resulting bioactive material. Various heating methods can be utilized to provide this heating profile, such as forced convection in a kiln, heating the object directly in a flame, laser, or other focused heating methods. In this embodiment, the focused heating method is a secondary heating method that supplements a primary heating method, such as a kiln or oven heating apparatus. The secondary heating method provides the brief thermal excursion to the bond formation temperature, with a fast recovery to a temperature less than the glass transition temperature in order to avoid devitrification of the resulting three-dimensional matrix 110.

In an embodiment of the invention, combustion of the pore former 240 can be used to provide rapid and uniform heating throughout the object as a secondary heating method during the bond formation step 330. In this embodiment, the pore former 240 is a combustible material, such as carbon or graphite, or polymers, such as polymethyl methacrylate, that exothermically oxidize at elevated temperatures. The curing step 280 would initially heat in an inert or stagnant air kiln or oven environment to burn out any binder 230 materials. The pore former removal step 340 is controlled by the environment by purging with an inert gas, such as nitrogen, until the temperature is greater than the combustion temperature of the pore former, and nearly that of the desired bond formation temperature. Oxygen is introduced at the high temperature, so that when the pore former oxidizes, the temperature of the non-volatile materials can be locally increased at or above the glass transition temperature, or the bond formation temperature, until the pore former is fully combusted. At that point, the temperature can be reduced to avoid devitrification and/or the growth of grain boundaries of and within the resulting structure.

In yet another embodiment of the invention, the curing step 280 can be performed using a primary heat source, such as a kiln or oven, with a secondary heat source supplementing the kiln or oven to rapidly and uniformly heat the object to the desired temperature for the bond formation step to control the degree of crystallinity that would occur as a function of time and temperature. In this embodiment, a flame heat source can be applied directly to the object while it is in the kiln or oven.

The bonds formed between overlapping and adjacent nodes of the intertangled fibers forming the three-dimensional matrix 110 can be glass bonds having a composition substantially the same as the composition of the bulk fibers 210. The bonds can also be the result of a reaction between the bulk fibers 210 and the bonding agent 220 to form a glass bond having a composition that is substantially different than the composition of the bulk fiber 210. Due to the regulatory requirements relating to the approval of materials for use as a medical device or implant, it may be desirable to use approved material compositions as raw materials that are not significantly altered by the device fabrication methods and processes. Alternatively, it may be desirable to use raw materials that are precursors to an approved material composition, that form the desired composition during the device fabrication methods and processes. The present invention provides a bioactive and resorbable tissue scaffold device that can be either fabricated using a variety of medically approved materials, or fabricated into a medically-approved material composition.

The resorbable tissue scaffolds of the present invention can be used in procedures such as an osteotomy (for example in the hip, knee, hand and jaw), a repair of a structural failure of a spine (for example, an intervertebral prosthesis, lamina prosthesis, sacrum prosthesis, vertebral body prosthesis and facet prosthesis), a bone defect filler, fracture revision surgery, tumor resection surgery, hip and knee prostheses, bone augmentation, dental extractions, long bone arthrodesis, ankle and foot arthrodesis, including subtalar implants, and fixation screws pins. The resorbable tissue scaffolds of the present invention can be used in the long bones, including, but not limited to, the ribs, the clavicle, the femur, tibia, and fibula of the leg, the humerus, radius, and ulna of the arm, metacarpals and metatarsals of the hands and feet, and the phalanges of the fingers and toes. The resorbable tissue scaffolds of the present invention can be used in the short bones, including, but not limited to, the carpals and tarsals, the patella, together with the other sesamoid bones. The resorbable tissue scaffolds of the present invention can be used in the other bones, including, but not limited to, the cranium, mandible, sternum, the vertebrae and the sacrum. In an embodiment, the tissue scaffolds of the present invention have high load bearing capabilities compared to conventional devices. In an embodiment, the tissue scaffolds of the present invention require less implanted material compared to conventional devices. Furthermore, the use of the tissue scaffold of the present invention requires less ancillary fixation due to the strength of the material. In this way, the surgical procedures for implanting the device are less invasive, more easily performed, and do not require subsequent surgical procedures to remove instruments and ancillary fixations.

Figure 8:
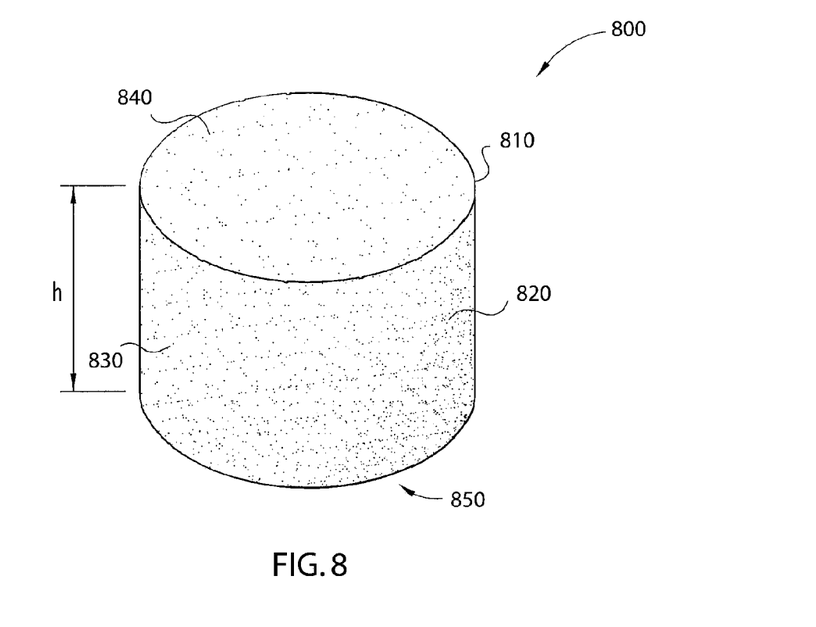
FIG. 8 is a side elevation view of a bioactive tissue scaffold according to the present invention manufactured into a spinal implant.
Figure 9:
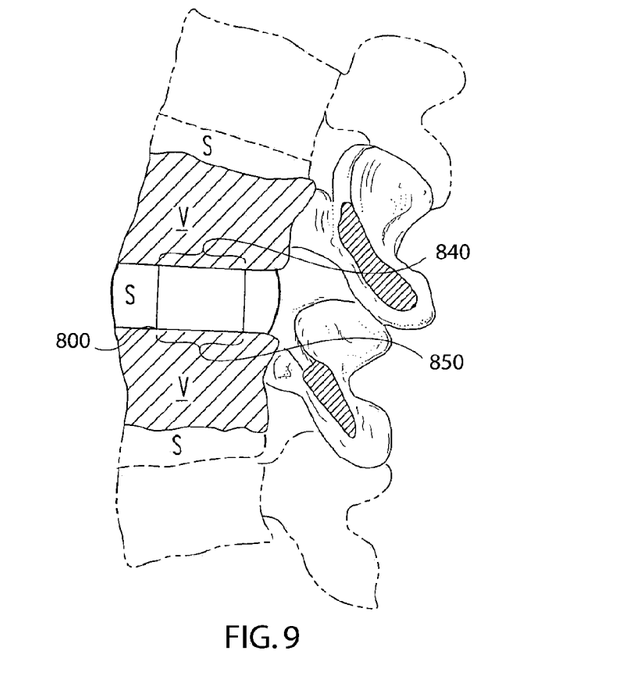
FIG. 9 is a side perspective view of a portion of a spine having the spinal implant of FIG. 8 implanted in the intervertebral space.

In one specific application, a tissue scaffold of the present invention, fabricated as described above, can be used as a spinal implant 800 as depicted in FIG. 8 and FIG. 9. Referring to FIG. 8 and FIG. 9, the spinal implant 800 includes a body 810 having a wall 820 sized for engagement within a space S between adjacent vertebrae V to maintain the space S. The device 800 is formed from bioactive glass fibers that can be formed into the desired shape using extrusion methods to form a cylindrical shape that can be cut or machined into the desired size. The wall 820 has a height h that corresponds to the height H of the space S. In one embodiment, the height h of the wall 820 is slightly larger than the height H of the intervertebral space S. The wall 820 is adjacent to and between a superior engaging surface 840 and an inferior engaging surface 850 that are configured for engaging the adjacent vertebrae V as shown in FIG. 9.

Figure 10:
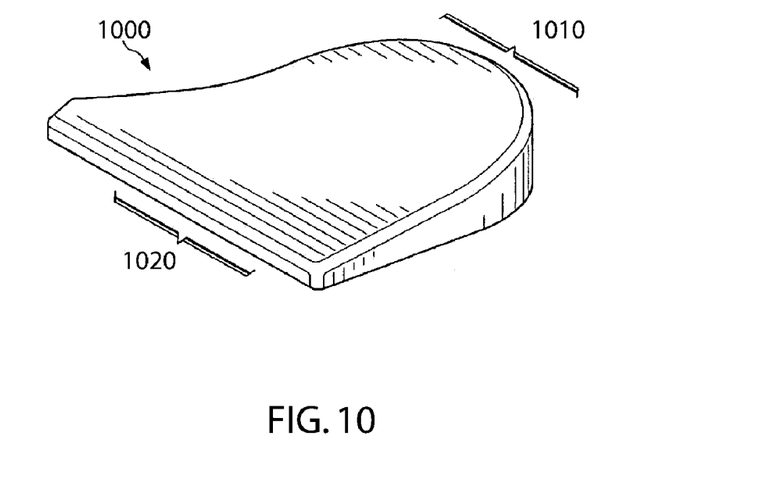
FIG. 10 is a schematic drawing showing an isometric view of a bioactive tissue scaffold according to the present invention manufactured into an osteotomy wedge.
Figure 11:
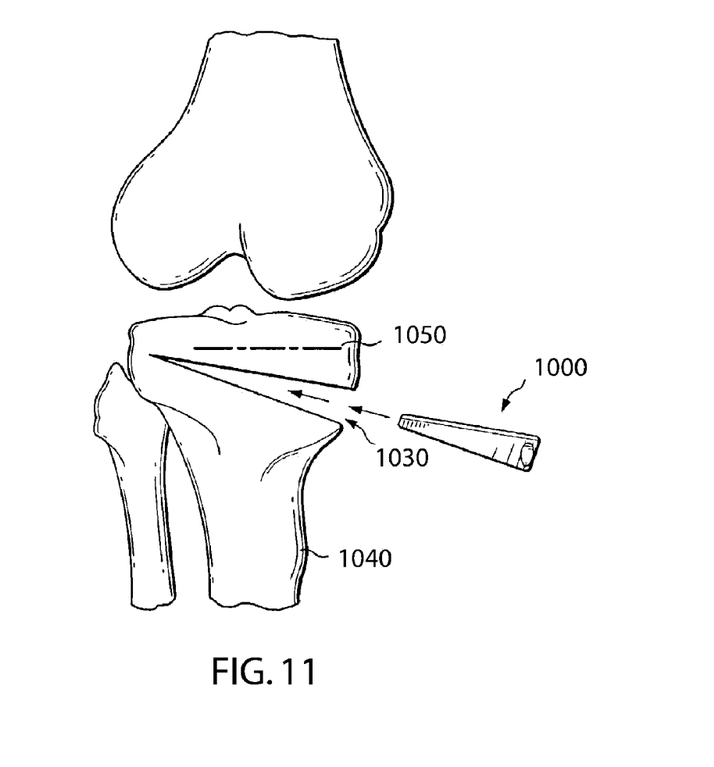
FIG. 11 is a schematic drawing showing an exploded view of the osteotomy wedge of FIG. 10 operable to be inserted into an osteotomy opening in a bone.

In another specific application, a tissue scaffold of the present invention, fabricated as described above, can be used as an osteotomy wedge implant 1000 as depicted in FIGS. 10 and 11. Referring to FIG. 10 and FIG. 11, the osteotomy implant 1000 may be generally described as a wedge designed to conform to an anatomical cross section of, for example, a tibia, thereby providing mechanical support to a substantial portion of a tibial surface. The osteotomy implant is formed from bioactive glass fibers bonded and fused into a porous material that can be formed from an extruded rectangular block, and cut or machined into the contoured wedge shape in the desired size. The proximal aspect 1010 of the implant 1000 is characterized by a curvilinear contour. The distal aspect 1020 conforms to the shape of a tibial bone in its implanted location. The thickness of the implant 1000 may vary from about five millimeters to about twenty millimeters depending on the patient size and degree of deformity. Degree of angulation between the superior and inferior surfaces of the wedge may also be varied.

FIG. 11 illustrates one method for the use of the osteotomy wedge implant 1000 for realigning an abnormally angulated knee. A transverse incision is made into a medial aspect of a tibia while leaving a lateral portion of the tibia intact and aligning the upper portion 1050 and the lower portion 1040 of the tibia at a predetermined angle to create a space 1030. The substantially wedge-shaped implant 1000 is inserted in the space 1030 to stabilize portions of the tibia as it heals into the desired position with the implant 1000 dissolving into the body as herein described. Fixation pins may be applied as necessary to stabilize the tibia as the bone regenerates and heals the site of the implant.

Generally, the use of a resorbable bone tissue scaffold of the present invention as a bone graft involves surgical procedures that are similar to the use of autograft or allograft bone grafts. The bone graft can often be performed as a single procedure if enough material is used to fill and stabilize the implant site. In an embodiment, fixation pins can be inserted into the surrounding natural bone, and/or into and through the resorbable bone tissue scaffold. The resorbable bone tissue scaffold is inserted into the site and fixed into position. The area is then closed up and after a certain healing and maturing period, the bone will regenerate and become solidly fused.

The use of a resorbable bone tissue scaffold of the present invention as a bone defect filler involves surgical procedures that can be performed as a single procedure, or multiple procedures in stages or phases of repair. In an embodiment, a resorbable tissue scaffold of the present invention is placed at the bone defect site, and attached to the bone using fixation pins or screws. Alternatively, the resorbable tissue scaffold can be externally secured into place using braces. The area is then closed up and after a certain healing and maturing period, the bone will regenerate to repair the defect.

EXAMPLES

The following examples are provided to further illustrate and to facilitate the understanding of the disclosure. These specific examples are intended to be illustrative of the disclosure and are not intended to be limiting in an way.

In a first exemplary embodiment a resorbable scaffold is formed from 13-93 fiber by mixing 75 grams of 13-93 fiber having an average diameter of approximately 34 μm obtained from Mo-Sci Corporation, Rolla, Mo. 65401, in bulk form, as the non-volatile components with 16 grams of HPMC as an organic binder and 20 grams of PMMA with a particle size of 25-30 μm as a pore former and approximately 40 grams of deionized water, adjusted as necessary to provide a plastically formable mixture. The mixture was extruded into a 14 mm diameter rod and dried in a microwave dryer. The volatile components were burned out in an air-purged oven and then heat treated at 720° C. for one hour to bond and fuse the 13-93 fiber into the bioresorbable tissue scaffold. The porosity for this example was measured to be 69.4%.

In a second exemplary embodiment a resorbable scaffold is formed from 13-93 fiber by mixing 5 grams of 13-93 fiber having an average diameter of approximately 34 μm obtained from Mo-Sci Corporation, Rolla, Mo. 65401, in bulk form, and 1 gram of 13-93 bioactive glass in a powder form (also from Mo-Sci Corporation) as the nonvolatile components with 2 grams of HPMC as an organic binder and 5 grams of PMMA with a particle size of 25-30 μm as a pore former and approximately 8 grams of deionized water, adjusted as necessary to provide a plastically formable mixture. The mixture was extruded into a 14 mm diameter rod, and dried in a microwave dryer. The volatile components were burned out in an air-purged oven and heat treated at 690° C. for 45 minutes to bond and fuse the 13-93 fiber into the bioresorbable tissue scaffold using the bioactive glass material to coat the adjacent and overlapping fiber with glass. The porosity for this example was measured to be 76%.

In a third exemplary embodiment a resorbable scaffold is formed from 13-93 fiber by mixing 5 grams of 13-93 fiber having an average diameter of approximately 34 μm obtained from Mo-Sci Corporation, Rolla, Mo. 65401, in bulk form, and 2 grams of 13-93 bioactive glass in a powder form (also from Mo-Sci Corporation) as the nonvolatile components with 2 grams of HPMC as an organic binder and 5 grams of 4015 graphite powder from Asbury Carbons, Asbury, N.J. with a distribution of particle sizes of between 150 to 425 μm as a pore former and approximately 10 grams of deionized water, adjusted as necessary to provide a plastically formable mixture. The mixture was extruded into a 14 mm diameter rod and dried for 30 minutes at 125° C. The volatile components were burned out in an air-purged oven and heat treated at 800° C. for 45 minutes to bond and fuse the 13-93 fiber into the bioresorbable tissue scaffold using the bioactive glass material to coat the adjacent and overlapping fiber with glass. The porosity for this example was measured to be 66.5% with a compressive strength of 7.0 MPa.

In a fourth exemplary embodiment a resorbable scaffold is formed from a mixture of 45S5 fiber and 13-93 fiber by mixing 45 grams of 13-93 fiber having an average diameter of approximately 34 μm obtained from Mo-Sci Corporation, Rolla, Mo. 65401, in bulk form with 30 grams of 45S5 fiber having an average diameter of 14 μm, (also from Mo-Sci Corporation) as the nonvolatile components with 16 grams of HPMC as an organic binder and 20 grams of potato starch having an average particle size of 50 μm as a pore former and approximately 40 grams of deionized water, adjusted as necessary to provide a plastically formable mixture. The mixture was extruded into a 14 mm diameter rod and dried in a microwave dryer. The volatile components were burned out in an air-purged oven and heat treated at 715° C. for 1 hour to bond and fuse the 13-93 and 45S5 fiber into the bioresorbable tissue scaffold with glass material from the fibers coating the adjacent and overlapping fiber. The porosity for this example was determined to be 40.4%

In a fifth exemplary embodiment a resorbable scaffold is formed from 13-93 fiber by mixing 5 grams of 13-93 fiber having an average diameter of approximately 34 μm obtained from Mo-Sci Corporation, Rolla, Mo. 65401, in bulk form, and 2 grams of 13-93 bioactive glass in a powder form (also from Mo-Sci Corporation) as the nonvolatile components with 2 grams of HPMC as an organic binder and 1.5 grams of PMMA with a particle size of 100 μm as a pore former and approximately 7 grams of deionized water, adjusted as necessary to provide a plastically formable mixture. The mixture was extruded into a 14 mm diameter rod and dried in a microwave dryer. The volatile components were burned out in an air-purged oven and heat treated at 680° C. for 45 minutes to bond and fuse the 13-93 fiber into the bioresorbable tissue scaffold using the bioactive glass material to coat the adjacent and overlapping fiber with glass. The porosity for this example was measured to be 58.5% with a compressive strength of 4.7 MPa.

In a sixth exemplary embodiment a resorbable scaffold is formed from 13-93 fiber by mixing 5 grams of 13-93 fiber having an average diameter of approximately 34 μm obtained from Mo-Sci Corporation, Rolla, Mo. 65401, in bulk form as the nonvolatile components with 2 grams of HPMC as an organic binder and 1.5 grams of PMMA with a particle size of 100 μm as a pore former and approximately 8 grams of deionized water, adjusted as necessary to provide a plastically formable mixture. The mixture was extruded into a 14 mm diameter rod and dried in a microwave dryer. The volatile components were burned out in an air-purged oven and heat treated at 700° C. for 90 minutes to bond and fuse the 13-93 fiber into the bioresorbable tissue scaffold using bioactive glass material from the fiber to coat the adjacent and overlapping fiber with glass. The porosity for this example was measured to be 47.0% with a compressive strength of 22.5 MPa.

In a seventh exemplary embodiment a resorbable scaffold is formed from 13-93 fiber by mixing 5 grams of 13-93 fiber having an average diameter of approximately 34 μm obtained from Mo-Sci Corporation, Rolla, Mo. 65401, in bulk form, and 3 grams of 13-93 bioactive glass in a powder form (also from Mo-Sci Corporation) as the nonvolatile components with 2 grams of HPMC as an organic binder and 5 grams of PMMA with a particle size of 25-30 μm as a pore former and approximately 8 grams of deionized water, adjusted as necessary to provide a plastically formable mixture. The mixture was extruded into a 14 mm diameter rod and dried in a microwave dryer. The volatile components were burned out in an air-purged oven and heat treated at 710° C. for 45 minutes to bond and fuse the 13-93 fiber into the bioresorbable tissue scaffold using the bioactive glass material to coat the adjacent and overlapping fiber with glass. The porosity for this example was measured to be 50.2% with a compressive strength of 20.1 MPa.

A method of filling a defect in a bone includes filling a space in the bone with a resorbable tissue scaffold comprising bioactive fibers bonded into a porous matrix, the porous matrix having a pore size distribution to facilitate in-growth of bone tissue; and attaching the resorbable tissue scaffold to the bone.

A method of treating an osteotomy includes filling a space in the bone with a resorbable tissue scaffold comprising bioactive fibers bonded into a porous matrix, the porous matrix having a pore size distribution to facilitate in-growth of bone tissue; and attaching the resorbable tissue scaffold to the bone.

A method of treating a structural failure of a vertebrae includes filling a space in the bone with a resorbable tissue scaffold comprising bioactive fibers bonded into a porous matrix, the porous matrix having a pore size distribution to facilitate in-growth of bone tissue; and attaching the resorbable tissue scaffold to the bone.

A method of fabricating a synthetic bone prosthesis includes mixing bioactive fiber with a binder, a pore former and a liquid to provide a plastically formable batch; kneading the formable batch to distribute the bioactive fiber with the pore former and the binder, the formable batch a homogeneous mass of intertangled and overlapping bioactive fiber; forming the formable batch into a desired shape to provide a shaped form; drying the shaped form to remove the liquid; heating the shaped form to remove the binder and the pore former; and heating the shaped form to a bond formation temperature using a primary heat source and a secondary heat source to form bonds between the intertangled and overlapping bioactive glass fiber.

In an embodiment, the present invention discloses use of bioactive fibers bonded into a porous matrix, the porous matrix having a pore size distribution to facilitate in-growth of bone tissue for the treatment of a bone defect.

In an embodiment, the present invention discloses use of bioactive fibers bonded into a porous matrix, the porous matrix having a pore size distribution to facilitate in-growth of bone tissue for the treatment of an osteotomy.

In an embodiment, the present invention discloses use of bioactive fibers bonded into a porous matrix, the porous matrix having a pore size distribution to facilitate in-growth of bone tissue for the treatment of a structural failure of various parts of a spinal column.

The present invention has been herein described in detail with respect to certain illustrative and specific embodiments thereof, and it should not be considered limited to such, as numerous modifications are possible without departing from the spirit and scope of the appended claims.

What is claimed is:

1. A resorbable three-dimensional tissue scaffold comprising:
   bioactive glass fibers;
   bioactive glass bonding to at least a portion of the bioactive glass fibers; and
   pore space within the three-dimensional tissue scaffold by volatile components removed during the bioactive glass bonding to the bioactive glass fibers,
   wherein the pore space creates a porosity between about 40% and about 85% in the resorbable three-dimensional tissue scaffold.

2. tissue scaffold according to claim 1 wherein the pore space within the three-dimensional tissue scaffold has a pore size between about 100 µm and about 500 µm.

3. The tissue scaffold according to claim 2 wherein the pore size has a bi-modal size distribution.

4. The tissue scaffold according to claim 1 wherein a plurality of the bioactive glass fibers are bonded to adjacent bioactive glass fibers providing bundles of bonded bioactive glass fibers.

5. The tissue scaffold according to claim 1 wherein the bioactive glass fibers comprise sodium carbonate, calcium carbonate, phosphorus pentoxide, about 45 mol % to about 60 mol % silica, and an about 2 to an about 10 molar ratio of calcium to phosphate.

6. The tissue scaffold according to claim 1 wherein the bioactive glass fibers comprise glass fiber having a composition in respective mol % quantities of 6% $Na_2O$; 7.9% $K_2O$; 7.7% MgO; 22.1% CaO; 0% $B_2O_3$; 1.7% $P_2O_5$; and 54.6% $SiO_2$.

7. The tissue scaffold according to claim 1 wherein the bioactive glass fibers have a diameter ranging from about 1 µm to about 200 µm.

8. The tissue scaffold according to claim 7 wherein the bioactive glass fibers have a diameter ranging from about 5 µm to about 100 µm.

9. A bioactive tissue scaffold comprising:
   a rigid three-dimensional matrix of a bioactive composition formed from a process comprising:
   mixing a bioactive fiber, a binder, a bioactive glass powder bonding agent, a pore former, and a liquid into a plastically formable batch;
   forming the plastically formable batch into a shaped object;
   drying the shaped object to remove the liquid;
   removing the binder;
   removing the pore former; and
   heating the shaped object to fuse and bond the bioactive fiber into the rigid three-dimensional matrix using the bioactive glass powder bonding agent with pore space defined by the pore former.

10. The bioactive tissue scaffold according to claim 9 wherein the bioactive glass powder bonding agent is the same composition as the bioactive fiber.

11. The bioactive tissue scaffold according to claim 9 wherein the bioactive fiber comprises sodium carbonate, calcium carbonate, phosphorus pentoxide, about 45 mol % to about 60 mol % silica and an about 2 to an about 10 molar ratio of calcium to phosphate.

12. The bioactive tissue scaffold according to claim 9 wherein the bioactive fiber comprises a mixture of bioactive fiber having different compositions.

13. The bioactive tissue scaffold according to claim 9 wherein the bioactive glass powder bonding agent has a particle size between about 1 to about 1000 times smaller than the diameter of the bioactive glass fiber.

14. The bioactive tissue scaffold according to claim 9 wherein the pore former has a particle size between about 0.1 and about 100 times the bioactive fiber diameter.

* * * * *

UNITED STATES PATENT AND TRADEMARK OFFICE
CERTIFICATE OF CORRECTION

PATENT NO. : 8,337,876 B2
APPLICATION NO. : 12/832391
DATED : December 25, 2012
INVENTOR(S) : James Jenq Liu et al.

It is certified that error appears in the above-identified patent and that said Letters Patent is hereby corrected as shown below:

In the Claims

Claim 2, line 1, "tissue scaffold" should read -- The tissue scaffold --

Signed and Sealed this
Fourteenth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,337,876 B2  
APPLICATION NO. : 12/832391  
DATED : December 25, 2012  
INVENTOR(S) : James Jenq Liu et al.

Page 1 of 1

It is certified that error appears in the above-identified patent and that said Letters Patent is hereby corrected as shown below:

In the Claims

Column 19, line 54 (Claim 2, line 1) "tissue scaffold" should read -- The tissue scaffold --

This certificate supersedes the Certificate of Correction issued May 14, 2013.

Signed and Sealed this
Eleventh Day of June, 2013

Teresa Stanek Rea
*Acting Director of the United States Patent and Trademark Office*